| United States Patent [19] | [11] | 4,283,392 |
|---|---|---|
| Dietze et al. | [45] | Aug. 11, 1981 |

[54] INFUSION SOLUTIONS CONTAINING AMINO ACIDS AND MINERAL SALTS

[75] Inventors: Günther Dietze; Matthias Wicklmayr, both of Munich, Fed. Rep. of Germany

[73] Assignee: THERA Gesellschaft fur Patentverwertung mbH, Fed. Rep. of Germany

[21] Appl. No.: 114,241

[22] Filed: Jan. 22, 1980

[30] Foreign Application Priority Data

Jan. 23, 1979 [CH] Switzerland .............................. 644/79

[51] Int. Cl.³ ............................................. A61K 37/00
[52] U.S. Cl. ................................................... 424/177
[58] Field of Search ......................................... 424/177

[56] References Cited

PUBLICATIONS

Chem. Abst., 89-37120c (1978).

*Primary Examiner*—Stanley J. Friedman
*Attorney, Agent, or Firm*—Burns, Doane, Swecker & Mathis

[57] ABSTRACT

There are provided infusion solutions for a low-caloric parenteral nutrition which contain 10 to 200 grams (preferably 50 to 100 grams) of essential and non-essential amino acids as well as 50 to 10,000 μg (200 to 1000 μg) of kinin per one liter of infusion solution, and mineral salts.

5 Claims, No Drawings

INFUSION SOLUTIONS CONTAINING AMINO ACIDS AND MINERAL SALTS

BACKGROUND OF THE INVENTION

It is known that the human organism will unrestrictedly activate proteins in all tissues when in a state of stress, for example after surgery or an injury, in order to metabolize and to utilize as a supply of energy the amino acids which are present therein. One portion of the mobilized amino acids will be oxidatively degraded in the course of this process within the peripheral tissues because these tissues do not have sufficient energy substrates in this case of increased conversion during the state of stress and the liberation of the aliphatic acids from the depot fats will take its course only after some delay. Since the amino acids are derived not only from the tissues, for example the muscle, but also from functionally important proteins, there exists the danger of functional disturbances which will then become noticeable during the period following surgery, for example by an increase in the rate of infections.

For this reason, the patient will usually be fed parenterally after surgery or a major injury, which means that he is being supplied intravenously with energy substrates as a means to overcome this deficiency of body-produced substrates and to preserve the valuable amino acids within the organism. However, in order to successfully replace the amino acids in their function of burning of the cells, a substantial supply of energy-rich substrates will be necessary, in other words, a high-caloric parenteral feeding. Since a state of stress also disturbs the glucose utilization, the replacement of the deficient energy substrates by glucoses only will result in relatively high glucose level ratios, as experienced for example in the case of diabetics, so that this treatment could lead to hyperosmotic conditions or even hyperosmotic coma. In view of this, the glucose has been replaced partially by sugar substitutes, fat-emulsions and alcohols. Unfortunately, these substrates which are suitable energy-providing substrates have other undesirable side-effects rendering these substances only conditionally suitable for a complete parenteral feeding. The sugar substitutes interfere with the energy metabolism of the liver while the fat-emulsions adversely influence the body resistance to infections, and the alcohol influence the fat- and the uric acid metabolism of the liver, causing liver damages, infections and gout.

A definite improvement in energy replenishment in such situations has been attained by the admixture of kinins to glucose-containing infusion solutions of high percentages The published German patent application No. 26 57 381 describes such infusion solutions containing 100 to 300 grams of glucose and 1 $\mu$g to 1.6 mg of kinins per liter and possibly some other infusion components. Dietze et al have published reports on the influence of Brady kinin or the kallikreinekinin system, respectively, on the glucose utilization in the muscle in "Klin. Wochenschrift", vol. 55, page 1357 (1972) and in Hoppe Seyler's "Z. Physiol. Chem.", vol. 358, page 633 (1977). Wicklmayr et al also reported an improvement of the poor glucose utilization by the use of Brady kinin in the case of diabetics and patients under stress caused by surgery, see "Klinische Wochenschrift", vol. 56, pages 1077 to 1083 (1978). These authors believe that this effect is due to a stimulation of the glucose transport by way of the cellular membrane of the muscle tissue so that the glucose is being utilized more effectively, thus preventing the occurrence of hyperosmotic conditions. The cell will then not require any other energy substrates, and especially not amino acids, fat or alcohol. The amino acids, originating from body-produced proteins and possibly augmented by the glucose-containing infusion solutions of the DE-OS No. 26 57 381, are therefore fully available for the closing of the defect at the area of the bodily injury (for example resulting from surgery).

It was thus possible by means of the thus described infusion therapy to influence the protein metabolism by replacing with glucose the amino acids content which had been mobilized from the protein-containing tissues and utilized for the energy-production of the cell. However, this method did not guarantee that amino acids would not be mobilized from the protein-containing body tissues of the liver, muscles, nerves and brain because the organism continued the mobilization of amino acids with the aid of the catabolic hormones which reduced the anabolic effect of insulin on the protein metabolism in order to make them available to protect the defect of the organism at the area of injury (for example resulting from surgery). This resulted in the disadvantage for the patient that, in spite of the infusion therapy being employed, in addition to the nerve and muscle proteins, the very valuable functional proteins of the blood which are actively taking part in specific functions of the body, for example in the coagulation, the protection against infection and the like, were included in the combustion process.

OBJECTS AND SUMMARY OF THE INVENTION

Accordingly, a general object of the present invention is to avoid or substantially alleviate the above problems of the prior art.

A more specific object of the present invention is to provide an amino acid- and kinin-containing infusion composition.

Another object of the present invention is to provide an amino acid- and kinin containing infusion composition which is especially useful for low caloric parenteral nutrition.

Other objects and advantages of the invention will become apparent from the following summary and description of the preferred embodiments of the present invention.

The present invention provides an infusion solution containing amino acids and mineral salts for a low caloric parenteral nutrition comprising 10 to 200 grams of essential and non-essential amino acids per liter of solution and 50 to 10,000 $\mu$g of kinin per liter of solution and the treatment of a patient with such a solution.

DETAILED DESCRIPTION OF THE INVENTION

It has now been found unexpectedly and surprisingly that the protein metabolism can be influenced more advantageously and properly than by the presently used infusion therapy if for the purpose of the parenteral feeding approximately 1,000 calories are replaced only by amino acids and the amino acids are administered with the aid of an amino acid mixture and a specific quantity of kinin without large amounts of additional energy substrates such as glucose or sugar alcohols, considered necessary heretofore, resulting in a fully balanced nitrogen equilibrium. This normalization of the amino acid metabolism in this catabolic situation comes about because the body-produced amino acids are replaced by the exogenously administered amino acids for the combustion in the cells and the kinin, in conjunction with a large supply of amino acid, intensifies the body-protein-preserving effect of the insulin with the catabolic hormones thereby preventing the proteolysis within the body tissues, and where the amino acids, not mobilized any longer from the protein, are replaced by the amino acids which are present in the amino acid infusion solution. It becomes thus possible for the first time to preserve the depot proteins of the organism during a state of stress, for example after surgery or at the time of infection, without the need of providing a glucose supply which is undesirable for many patients.

These novel infusion solutions for a low-parenteral feeding contain 10 to 200, preferably 50 to 100, grams of essential and non-essential amino acids in usual combination as well as 50 to 10,000, preferably 200 to 1,000, µg of kinins per liter of infusion solution. The kinins especially suitable for these low-caloric solutions are the nonapeptide Brady kinin as well as the decapeptide kallidin. It is also possible to use a mixture of several kinins.

The solutions of the present invention are very stable and can be easily sterilized by means of heat. Due to the absence of the glucose, there is no danger that by-products will be formed.

It was generally believed heretofore that a nutrition very rich in calories (high-caloric nutrition) was necessary to build up the body-produced proteins and to inhibit the proteolysis in the case of stress resulting from surgery. It has now been found that the desired amino acid utilization can be accomplished by the presence of the kinins in the amino acid infusion solution even without a caloric increase of the nutrition. The novel parenteral feeding has the further important advantage that no high-molecular, hyperosmotic solutions are used so that the amino acid/kinin solutions, for example 5 or 10 percent solutions, can be injected into the peripheral vein. The known amino-acid-containing high-percentage glucose solutions required the often risky introduction of a central vein catheter into a large vein close to the heart in order to provide the organism with this hyperosmotic infusion solution.

The new method of parenteral feeding is particularly advantageous for patients with a congenital or acquired deficiency in glucose utilization, that is, for juvenile as well as adult diabetics because this new solution makes it possible to stop the extremely high protein catabolism which occurs in the case of diabetics when they are subjected to the above-discussed stress situations, without the danger of an unbalancing of the glucose metabolism always possible heretofore in the case of infusion of high-percentage glucose-containing solutions, especially because very large quantities of insulin could not practically be administered in view of the danger of hypoglycemia.

A patient can be given approximately 250 to 3000 ml of the amino acid solution of the present invention per day, depending on his specific needs, which is equivalent to a total quantity of 20 to 200 gram of amino acid and 0.6 to 3 mg of kinin, an amount which can be well tolerated by the body over a period of 24 hours.

Clinical tests of a group of eight patients which had been subjected to surgery showed a pronounced reduction in the nitrogen secretion in the urine if the amino-acid-containing infusion solution contains the Brady kinin as proposed by the invention. The tests were conducted from 12 to 72 hours after surgery. During this period the patients were given first a continuous drop-by-drop infusion with an approximately 5% amino acid solution as listed in the table below (infusion solution A) but without the Brady kinin, at a quantity of 2500 ml per 24 hours, and also electrolytes in accordance with conventional clinical requirements. The average nitrogen net secretion amounted to 4.8 gram of N in the period of 12 to 24 hours after surgery, and 5.6 gram of N in the period of 24 to 36 hours after surgery.

During the period of 24 to 48 hours after surgery Brady kinin in a quantity of 200 µg per liter was added to the amino acid infusion solution. Due to this admixture, the secretion of nitrogen dropped to 0.6 gram in the period of 36 to 48 hours after surgery and to 1.0 gram of nitrogen of 48 to 60 hours. When the Brady kinin admixture was discontinued, with the amino acid infusion administered free of kinins, the nitrogen secretion increased again to 4.9 gram per 12 hours, that is in the period of 60 to 72 hours after surgery. The results of the tests are an indication of a definite improvement in the amino acid utilization in the sense of an anabolic effect relating to the build-up of body-produced protein.

Another test arrangement further demonstrated that the presence of Brady kinin will improve the utilization of amino acid by the muscular cells. If the amino acid concentration is measured in the blood stream of an artery and in the blood stream of a vein at the human forearm, a definite decrease in the concentration of amino acid within the venous blood will occur when Brady kinin is continuously added to the arterial blood. This demonstrates again that under the influence of the kinin and without an additional glucose supply there occurs an increase in the amino acid uptake in the muscle cell, to be interpreted as a protein-anabolic effect.

The infusion solution of the invention also reduces the rate of decomposition of protein in the cells and in the blood serum of the patient which normally increases in the period after surgery.

The four infusion solutions A, B, C and D with an amino acid content of approxiamately 5, 10, 20 and 2 percent, respectively, are prepared by filling the substances listed in the table below and in the quantities given into standard infusion bottles which can be used immediately after being sterilized under heat. The solutions are for all practical purposes stable without any limitations and each may be used as an infusion solution in accordance with the purposes of the present invention.

| Example | Infusion solutions | | | |
|---|---|---|---|---|
| | A | B | C | D |
| Glutamic acid | 9.5 g | 19 g | 38 g | 4.5 g |
| Alanine | 6.5 | 13 g | 26 g | 3.0 g |
| Proline | 7.5 g | 15 g | 30 g | 3.5 g |
| Glycine | 9.0 g | 18 g | 36 g | — |
| Arginine | 3.5 g | 7.0 g | 14 g | 2.0 g |
| Histidine | 1.0 g | 2.0 g | 4.0 g | 0.5 g |
| Valine | 1.5 g | 3.0 g | 6.0 g | 0.75 g |
| Tryptophan | 0.5 g | 1.0 g | 2.0 g | 0.25 g |
| Threonine | 1.1 g | 2.2 g | 4.0 g | 0.5 g |
| Phenylanaline | 2.0 g | 4.5 g | 9.0 g | 1.1 g |
| Methionine | 2.0 g | 4.0 g | 8.0 g | 1.05 g |
| Lysine . HCl | 2.0 g | 4.5 g | 9.0 g | 1.25 g |
| Leucine | 2.0 g | 4.5 g | 9.0 g | 1.1 g |
| Isoleucine | 2.0 g | 3.0 g | 6.0 g | 0.8 g |

-continued

| Example | Infusion solutions | | | |
|---|---|---|---|---|
| | A | B | C | D |
| NaOH | 1.0 g | 1.5 g | 3.0 g | 1.6 g |
| KOH | 1.4 g | 1.6 g | 1.9 g | 1.68 g |
| Magnesiumacetate . 4H$_2$O | 1.0 g | 1.0 g | 1.0 g | 1.07 g |
| Sorbitol | — | — | — | 25 g |
| Xylitol | — | — | — | 25 g |
| Malic acid | 0.4 g | 0.7 g | 0.9 g | 3.0 g |
| Brady kinin | 200 µg | 200 µg | 400 µg | 350 µg |
| Distilled water . ad | 1000 ml | 1000 ml | 1000 ml | 1000 ml |

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. An infusion solution for low-caloric parenteral nutrition, comprising 10 to 200 grams of essential and non-essential amino acids per liter of solution, 50 to 10,000 µg of a kinin selected from the group consisting of Brady kinin, kallidin or mixtures thereof per liter of solution and mineral salts.

2. An infusion solution as defined in claim 1, containing from 50 to 100 grams of amino acids per liter of solution and from 200 to 1000 µg of kinins per liter of solution.

3. An infusion solution as defined in any one of claims 1 or 2, in which the kinin is Brady kinin.

4. An infusion solution as defined in claim 3 containing 100 to 5000 µg of Brady kinin per liter of solution.

5. A method of treating a patient to preserve the depot proteins which comprises parenteral administration to said patient of an effective amount of the infusion solution of claim 1.

* * * * *